United States Patent [19]

Silverberg et al.

[11] Patent Number: 5,459,248
[45] Date of Patent: Oct. 17, 1995

[54] PROCESS OF PREPARING ETOPOSIDE PHOSPHATE AND ETOPOSIDE

[75] Inventors: Lee J. Silverberg, Fayetteville; Purushotham Vemishetti, East Syracuse; John L. Dillon, Jr., Clay; John J. Usher, East Syracuse, all of N.Y.

[73] Assignee: Bristol-Myers Squibb Company, New York, N.Y.

[21] Appl. No.: 145,517

[22] Filed: Nov. 4, 1993

[51] Int. Cl.$^6$ ............................ A61K 31/70; C07H 15/24
[52] U.S. Cl. .................... 536/18.6; 536/4.1; 536/17.1; 536/115; 536/117; 536/120
[58] Field of Search ......................... 536/4.1, 17.1, 536/17.2, 18.1, 18.2, 18.7, 115, 117, 120; 514/27, 35

[56] References Cited

U.S. PATENT DOCUMENTS

| | | | |
|---|---|---|---|
| 2,666,778 | 1/1954 | Steinberg | 260/461 |
| 3,524,844 | 8/1970 | Keller-Juslen et al. | 260/210 |
| 4,564,675 | 1/1986 | Kurabayashi et al. | 536/18.1 |
| 4,757,138 | 7/1988 | Fujii et al. | 536/18.1 |
| 4,888,419 | 12/1989 | Saulnier et al. | 536/18.1 |
| 4,904,768 | 2/1990 | Saulnier et al. | 536/17.1 |
| 4,997,931 | 3/1991 | Ohnuma et al. | 514/27 |
| 5,036,055 | 7/1991 | Ohnuma et al. | 514/27 |
| 5,041,424 | 8/1991 | Saulnier et al. | 514/27 |
| 5,066,645 | 11/1991 | Ohnuma et al. | 514/27 |
| 5,081,234 | 1/1992 | Ohnuma et al. | 536/17.1 |
| 5,206,350 | 4/1993 | Wang et al. | 536/18.1 |

FOREIGN PATENT DOCUMENTS

| | | |
|---|---|---|
| 0456229 | 11/1991 | European Pat. Off. . |
| 0567089 | 4/1992 | European Pat. Off. . |
| 0511563 | 11/1992 | European Pat. Off. . |

*Primary Examiner*—Douglas W. Robinson
*Assistant Examiner*—Howard C. Lee
*Attorney, Agent, or Firm*—Samuel J. DuBoff

[57] ABSTRACT

Etoposide phosphate is prepared by coupling dibenzyl 4'-demethyl-4-epipodophyllotoxin-4'-phosphate with 2,3-di-O-benzyl-4,6-O-ethylidene-α,β-D-glucopyranose in a solvent and subsequently removing the protecting groups. The tetra-benzyl protected etoposide phosphate is recrystallized from methanol or directly crystallized from acetonitrile by adding methanol to yield substantially the pure C-1"-β form. The benzyl protecting groups are simultaneously removed by hydrogenation to produce etoposide phosphate in high yields. In a further embodiment, etoposide phosphate is treated with a phosphatase enzyme to yield etoposide.

33 Claims, No Drawings

PROCESS OF PREPARING ETOPOSIDE PHOSPHATE AND ETOPOSIDE

FIELD OF THE INVENTION

The present invention relates to a novel process for the preparation of antitumor compounds, and to the novel intermediates for preparing the antitumor compounds. More particularly, the invention is directed to a process for preparing 4'-demethylepipodophyllotoxin glucoside 4'-phosphates and the intermediate compounds for preparing the phosphates. The invention is particularly directed to a process for preparing etoposide phosphate and for preparing etoposide from etoposide phosphate.

BACKGROUND OF THE INVENTION

Etoposide and teniposide are 4'-demethylepipodophyllotoxin glucoside derivatives which are widely used in clinical therapy for treating cancer. In particular, etoposide is approved in the United States for treating small cell lung cancer and testicular cancer. However, etoposide exhibits limited solubility in water which makes it difficult to formulate into suitable pharmaceutical compositions.

To increase the water solubility of etoposide and its ability to be administered, etoposide phosphate is prepared as a prodrug. Etoposide phosphate metabolizes within the body to etoposide which can then be utilized by the body. One example of a water soluble prodrug is described in U.S. Pat. No. 4,904,768 which discloses water soluble prodrugs of 4'-demethylepipodophyllotoxin glucoside derivatives bearing a 4'-phosphate group. One example disclosed therein is etoposide 4'-phosphate. Etoposide 4'-phosphate is prepared by reacting etoposide with phosphorous oxychloride followed by hydrolysis, or by reacting etoposide with diphenyl chlorophosphate followed by hydrogenation to remove the phenyl groups.

The preparation of epipodophyllotoxin glycosides are also disclosed in U.S. Pat. No. 4,997,931. The 4'-demethylepipodophyllotoxin glycosides are prepared by condensing 4'-protected 4'-demethylepipodophyllotoxin with a protected sugar. The resulting compound is then derivatized to produce the corresponding 4'-phosphate.

The previous processes for preparing etoposide and etoposide phosphate typically require the protection of the phenol, coupling with a protected sugar and then the removal of the protecting groups. In addition, most of these methods require different protecting groups for the hydroxy and phosphate groups. The different protecting groups require multiple steps to remove respective protecting groups. The deprotection steps often require acid or alkaline conditions, which can degrade the final product, resulting in low yields.

Etoposide phosphate is usually prepared from etoposide by the additional steps of phosphorylation and deprotection. These multiple steps typically result in lower overall yields of the desired compounds as well as the expense and difficulty of producing the compounds due to undesirable phosphorylation of the glucosidic hydroxyls on etoposide.

SUMMARY OF THE INVENTION

The present invention is directed to a process of preparing 4'-demethylepipodophyllotoxin glucoside 4'-phosphates, and in particular etoposide phosphate by coupling a novel protected sugar with a novel protected 4'-demethyl-4-epi-podophyllotoxin-4'-phosphate. More particularly, the invention is directed to a di(arylmethyl)-protected sugar and a tetra-arylmethyl-protected 4'-demethyl-4-epipodophyllotoxin glucoside 4'-phosphate and a process of preparing etoposide phosphate therefrom. The arylmethyl protecting groups on the hydroxyl and phosphate groups may be the same or different, and are preferably benzyl or benzyl substituted with one or more selected from the group consisting of $C_{1-4}$ alkyl, hydroxy, phenyl, benzyl, halogen, alkoxy, nitro and carboxylic acids and esters thereof. The di(arylmethyl) 4'-demethyl-4-epipodophyllotoxin- 4'-phosphate is prepared by reacting the phenol with a di(arylmethyl) phosphite, a tetrahalomethane, a tertiary amine, and an acylation catalyst in a suitable solvent.

The protected sugar according to one embodiment of the invention is 2,3-di-O-benzyl-4,6-O-ethylidene-α,β-D-glucopyranose which is coupled with dibenzyl 4'-demethyl-4-epipodophyllotoxin phosphate in a solvent to produce the tetra benzyl protected etoposide phosphate. The protected etoposide 4'-phosphate is crystallized or recrystallized to recover the C-1"-β anomer. The protecting groups are removed simultaneously from the glycosidic and phosphate groups by hydrogenating or other suitable means to yield etoposide phosphate.

The overall process is efficient to yield etoposide 4'-phosphate in pure form without extensive purification steps. The protected dibenzyl-4-(2,3-di-O-benzyl-4,6-O-ethylidine-β -D-glucopyranosyl)-4'-dimethyl-4-epipodophyllotoxin- 4'-phosphate is easily crystallized from the reaction medium or recrystallized to isolate the C-1"-β form in substantially pure form. Isolation of the desired anomer is usually obtained in a single crystallization step.

Specifically, the invention is directed to a process for preparing a compound having the Formula Va

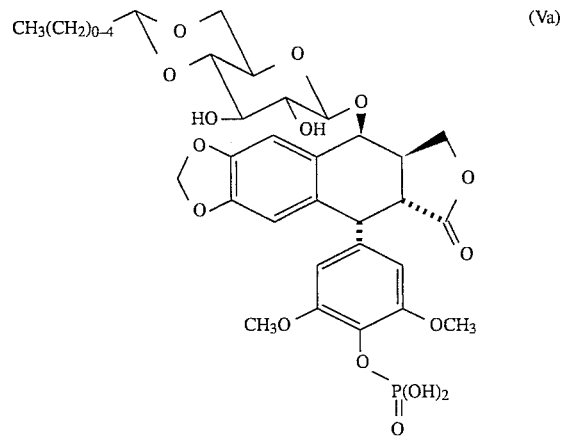

which comprises reacting a compound of Formula IIIb

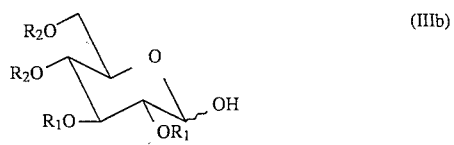

wherein $R_1$ is an arylmethyl hydroxy protecting group and $R_2$ is arylmethyl or the two $R_2$ groups together are $C_{1-5}$ alkylidene, with a compound of Formula II in a reaction medium in the presence of a Lewis acid

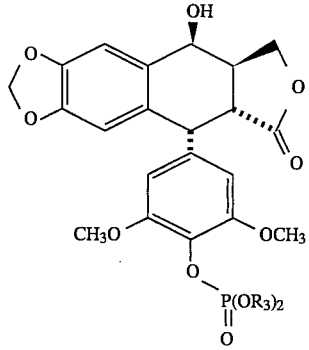
(II)

where $R_3$ is arylmethyl and where $R_1$, $R_2$ and $R_3$ are the same or different, to form the compound of Formula IVb

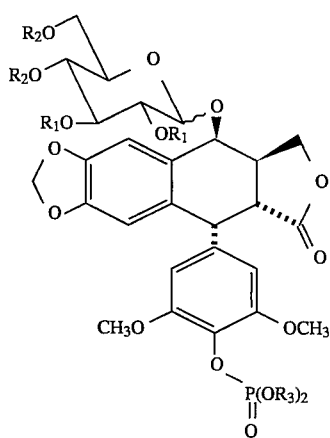
(IVb)

selectively crystallizing the C-1"-β anomer of Compound IVb and subsequently removing the hydroxy and phosphate protecting group, and in cases where $R_2$ is an arylmethyl hydroxy protecting group, reacting Compound IVb with a carbonyl having one to five carbon atoms or an acetal equivalent thereof.

A further aspect of the invention is a process of preparing a compound having the Formula VI

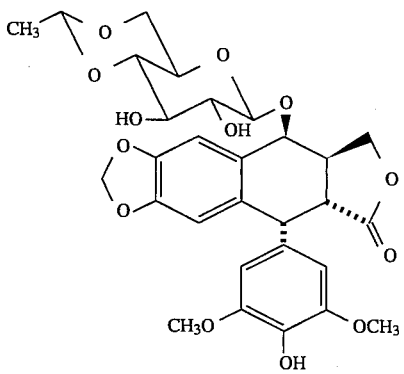
(VI)

which comprises reacting a compound of Formula V in a buffer solution

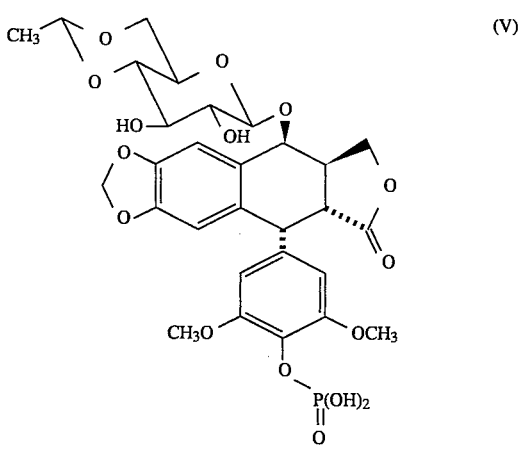
(V)

with a phosphatase enzyme to remove the phosphate, and recovering said compound of Formula VI.

Another aspect of the invention is to provide a process for preparing a compound of Formula VI

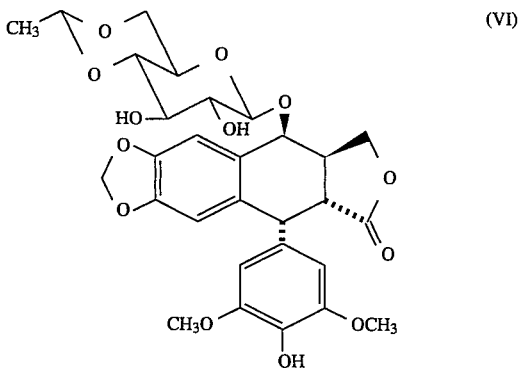
(VI)

comprising phosphorylating a compound of Formula I

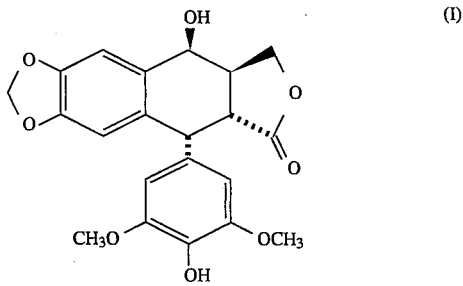
(I)

with a phosphorylating agent to produce a protected 4'-demethyl- 4-epipodophyllotoxin-4'-phosphate of Formula II

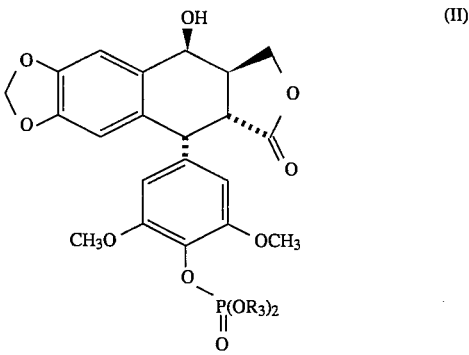
(II)

where $R_3$ is arylmethyl, reacting said compound of Formula II with a protected sugar of Formula III

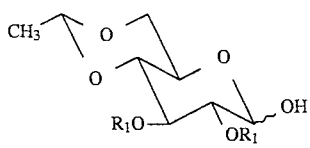

to produce a compound of Formula IV

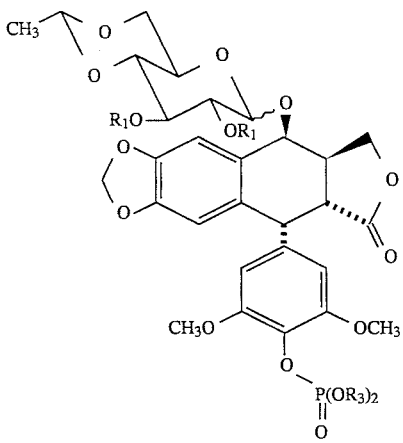

where $R_1$ is an arylmethyl protecting group; isolating the C-1″-β form of Formula IV; removing the hydroxy and phosphate protecting groups to produce a compound of Formula V

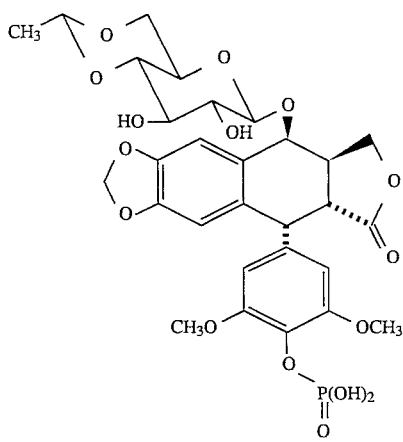

and treating said compound of Formula V with a phosphatase enzyme to remove the phosphate group and produce the compound of Formula VI.

DETAILED DESCRIPTION OF THE INVENTION

The present invention is directed to an improved process for preparing 4′-demethylepipodophyllotoxin glucoside 4′-phosphates and in particular etoposide 4′-phopshate, pharmaceutically acceptable salts, and solvates thereof. The invention is further directed to the preparation of arylmethyl protected sugars and arylmethyl protected precursors to etoposide and etoposide 4′-phosphate. The invention is further directed to a process of producing etoposide phosphate using hydroxy and phosphate protecting groups which allow easy separation of anomers by crystallization. A further advantageous feature is the ease by which the hydroxy and phosphate protecting groups can be removed simultaneously without degradation of the final product.

The process of the invention yields arylmethyl and, in particular, benzyl protected etoposide 4′-phosphate in a manner which can be easily separated to the anomerically pure C-1″-β form by crystallization from the reaction medium or by recrystallization from a suitable solvent. The overall process is rapid and efficient, providing an effective process for preparing etoposide 4′-phosphate. The phosphate group can be easily removed by a phosphatase enzyme providing an efficient process for preparing etoposide, pharmaceutically acceptable salts and solvates thereof.

The overall process is efficient for producing etoposide phosphate or etoposide as discussed in greater detail hereinafter. In a preferred embodiment, dibenzyl 4′-demethyl-4-epipodophyllotoxin-4,-phosphate is coupled in the presence of a Lewis acid with 2,3-dibenzyl-4,6-O-ethylidene-α,β-D-glucopyranose to produce an anomeric mixture of dibenzyl 4-(2,3-di-O-benzyl-4,6-O-ethylidene-α,β-D-glucopyranosyl)-4-demethyl-4-epipodophyllotoxin-4′-phosphate. The C-1″-β anomer has surprisingly been found to easily crystallize from solution in substantially pure form. The C-1″-β anomer may be directly crystallized from the reaction medium or recrystallized from a suitable solvent. The C-1″-β anomer is then recovered and hydrogenated to simultaneously remove the hydroxy and phosphate protecting groups.

As used herein, the term pharmaceutically acceptable salts include mono- and di-alkali metal salts, and alkaline earth metal salts. In preferred embodiments, the final compound is an ethanolate solvate. Solvates are formed by crystallization or recrystallization from organic solvents such as ethanol using standard procedures. The term alkylidene includes straight or branched alkyl chains including, for example, ethylidene, propylidene and isopropylidene.

In one aspect of the invention, the process leads to phosphorylation of 4′-demethylepipodophyllotoxin of Formula I to produce a protected di(arylmethyl) 4′-demethylepipodophyllotoxin- 4′-phosphate of Formula II. The phosphorylation process is preferably carried out by reacting 4′-demethylepipodophyllotoxin with di(arylmethyl) phosphite, a tetrahalomethane, a tertiary amine, and an acylation catalyst. The tetrahalomethane has the formula $CX_4$ where X is a halogen selected from the group consisting of F, Cl, Br and I. In preferred embodiments, the tetrahalomethane is $CCl_4$. The halogens on the carbon may be the same or different. The tertiary amine in preferred embodiments is N,N-diisopropylethylamine (DIPA), although other suitable tertiary amines may be used. The acylation catalyst may be a standard catalyst as known in the art. In preferred embodiments, the acylation catalyst is N,N-dimethylaminopyridine (DMAP). The reaction can be summarized as follows:

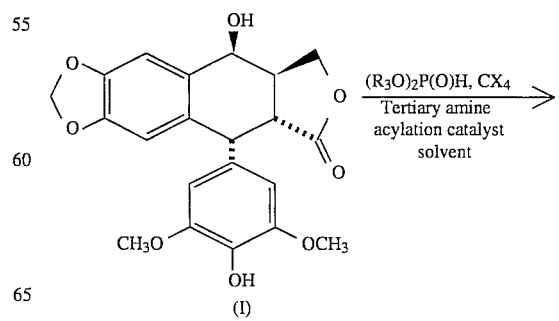

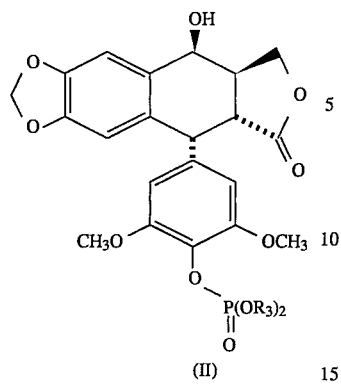

(II)

where $R_3$ is arylmethyl. In preferred embodiments, $R_3$ is benzyl whereby the resulting phosphate has the structure of Compound IIa.

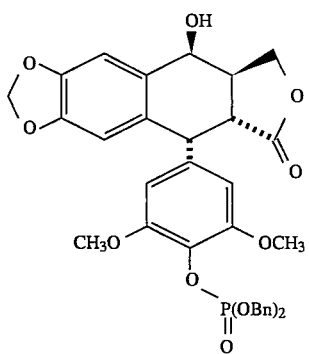

IIa

Alternatively, $R_3$ is a benzyl group substituted with one or more selected from the group consisting of $C_{1-4}$ alkyl, hydroxy, phenyl, benzyl, halogen, alkoxy, nitro and carboxylic acids and esters thereof. Suitable substituted benzyl groups include, for example, 2-methyl benzyl, 3-methyl benzyl, 4-methyl benzyl, 1 or 2-naphthyl, 2, 3 or 4-phenyl benzyl, 4-methoxycarbonyl benzyl, 2,6-dichlorobenzyl, 2-fluorobenzyl and pentafluorobenzyl.

This phosphorylation process is a convenient and easy process which produces the protected di(arylmethyl) 4'-demethylepipodophyllotoxin-4'-phosphate in high yield. The process is essentially a one pot process that is rapid and highly selective to the phenolic hydroxy group of Compound I. Although the process is particularly advantageous for the phosphorylation of 4'-demethylepipodophyllotoxin, the process is general and highly selective to phenols including, for example, p-fluorophenol, 2,6-dimethoxyphenol, 1,2-benzenediol and 4-hydroxyphenethyl alcohol. The process using 4-hydroxyphenethyl alcohol produced very little phosphorylation at the primary alcohol. Phosphorylation of etoposide gave the desired product with less glycosidic phosphorylation than with the preformed dibenzyl chlorophosphate.

The preferred solvent is acetonitrile, although any halogenated or non-halogenated solvent may be used in the phosphorylation. The tetrahalomethane and in particular carbon tetrachloride preferably is used only in reagent amounts rather than as a solvent as in some conventional processes. The amount of the tetrahalomethane used in the phosphorylation reaction is one or more equivalents per equivalent of the starting phenol. The reaction is also carried out under mild conditions at or below room temperature and typically below about $-10°$ C. The phosphorylation reaction is further carried out substantially in the absence of added dibenzylchlorophosphate (DBPCl) since DBPCl is generated in situ. This avoids the need to prepare DBPCl in a separate step and reduces the impurity content of the resulting phosphorylated product. Typically, the reaction proceeds to completion in about 45 minutes. Compound II is recovered by standard methods such as recrystallizing in isopropyl alcohol.

Compound II is then coupled with a hydroxy protected glucopyranose in the presence of a Lewis acid. In preferred embodiments, the Lewis acid is boron trifluoride etherate. Alternative Lewis acids include, for example, $AlCl_3$, $ZnCl_2$, $Et_2AlCl$, $CF_3SO_3H$, $CF_3SO_3Ag$, $Zn(CF_3SO_3)_2$ and $TMSCF_3SO_3$. The coupling reaction may be carried out in the presence of molecular sieves. The coupling reaction is carried out in a halogenated or non-halogenated solvent, most preferably acetonitrile. Other solvents include, for example, propionitrile, acetone, methylene chloride, chloroform, 1,2-dichloroethane and mixtures thereof.

A preferred hydroxy protected glucopyranose has the Formula III

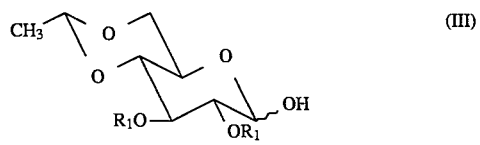

(III)

where $R_1$ is arylmethyl. In preferred embodiments, $R_1$ is benzyl such that the glucopyranose has the structure IIIa.

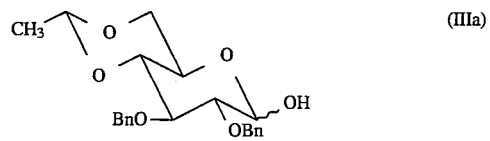

(IIIa)

In further embodiments, $R_1$ is a substituted benzyl that is substituted with one or more selected from the group consisting of $C_{1-4}$ alkyl, hydroxy, phenyl, benzyl, halogen such as fluoro, chloro, bromo and iodo, alkoxy, nitro and carboxylic acids and esters thereof. Suitable substituted benzyl groups include 2-methyl benzyl, 3-methyl benzyl, 4-methyl benzyl, 1 or 2-naphthyl, 2, 3 or 4-phenyl benzyl, 4-methoxy carbonyl benzyl, 2,6-dichlorobenzyl, 2-fluorobenzyl and pentafluorobenzyl. Typically, $R_1$ is the same as $R_3$.

The glucopyranose may further have the structure of Compound IIIb

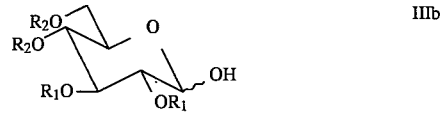

IIIb where $R_1$ is as above and $R_2$ is the same as $R_1$, or the two $R_2$ groups taken together are a $C_{1-5}$ alkylidene group. Preferably, the two $R_2$ groups together are ethylene. In alternative embodiments, the two $R_2$ groups together may be propylidene or isopropylidene.

Compounds III, IIIa and IIIb are prepared by known procedures such as that described in U.S. Pat. No. 4,997,931. The aryl protected glucopyranose is formed as an anomeric mixture of C-1-$\alpha,\beta$. Unlike most anomeric mixtures, the C-1-$\beta$ anomer of the arylmethyl glucopyranose can be separated from the $\alpha$ anomer by crystallization. Specifically, the anomeric mixture of the glucopyranose Compound IIIa can be crystallized from hexane to afford substantially anomerically pure C-1-$\beta$ form of Compound IIIa. Furthermore, the glucopyranose Compound IIIa having an initial $\beta:\alpha$ composition of 1:1 solidifies over time to a ratio of 85:15 $\beta:\alpha$.

The coupling reaction of the protected glucopyranose of Compound III with the protected 4'-demethyl-4-epipodophyllotoxin- 4'-phosphate of Compound II preferably is carried out in acetonitrile in the presence of a Lewis acid.

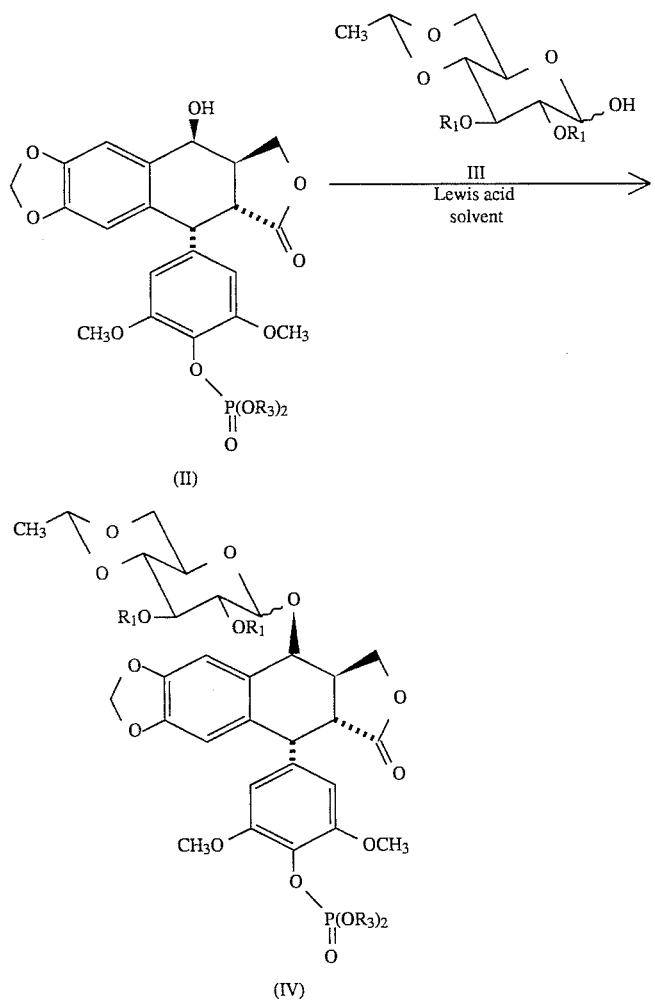

The coupling of the hydroxy protected glucopyranose of Compound IIIa with the dibenzyl 4'-demethyl-4-epipodophyllotoxin- 4'-phosphate (IIa) produces a C-1"-α,β anomeric mixture of dibenzyl 4-(2,3-di-O-benzyl-4,6-O-ethylidene-D-glucopyranosyl)- 4'-demethyl-4-epipodophyllotoxin- 4'-phosphate having the Formula IVa.

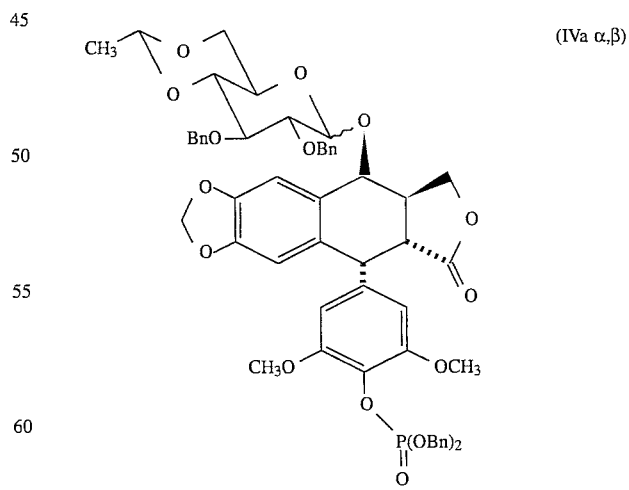

The coupling reaction proceeds rapidly and easily in the presence of boron trifluoride etherate to yield the α and β anomers of Compound IVa.

It is not necessary to isolate the D form of Compound III and particularly IIIa prior to the coupling. The final ratio of IVa α and IVa β does not depend on the anomeric composition of the starting Compound IIIa when the reaction is carried out in halogenated solvents. In acetonitrile, the coupling of Compounds IIa and IIIa (85:15 β:α) in the presence of boron trifluoride etherate at −20° C gives Compounds IVa β and IVa α in a ratio of 72:28. It is believed that the anomerization of the sugar occurs very rapidly in halogenated solvents, while anomerization is much slower in acetonitrile.

In further embodiments, a suitable salt may be added to the reaction mixture to increase the ionic strength of the solvent. Suitable salts include alkali and alkaline earth metal perchlorates. For example, the use of 0.5M LiClO$_4$ dissolved in acetonitrile increased the ratio of IVa β:α to 81:19.

The resulting anomeric mixture of Compound IVa α,β can be recrystallized from methanol to obtain substantially the pure C-1"-β form in high yields. A single crystallization in methanol or methanol in combination with other solvents crystallizes out the less polar IVa β anomer almost completely with substantially no contamination of the IVa α anomer.

The coupling reaction is generally carried out at or below room temperature and preferably at about −10° to −40° C. While the coupling reaction proceeds slower at lower temperatures, the lower temperatures favor the formation of the IVa C-1"-β anomer by slowing anomerization of IIIa in the reaction mixture. For example, the coupling reaction of dibenzyl 4'-demethyl-4-epipodophyllotoxin- 4'-phosphate and 2,3-di-O-benzyl-4,6-O-ethylidene-α ,β-D-glucopyranose (85:15 β:α) in acetonitrile at −20° C. produces the IVa β and IVa α in a ratio of 72:28, while at −40° C., the ratio is 74:26. The same coupling reaction in propionitrile at −20° C. results in a IVa β to IVa α ratio of 57:43, while at −78° C., the ratio is 76:24.

The preferred solvent for the coupling reaction is acetonitrile since the reaction proceeds rapidly compared to the standard solvents for coupling reactions. Acetonitrile has the unexpected property of enabling coupling reaction to reach completion in about two hours, while the reaction in dichloroethane takes about 18 hours. The coupling reaction in acetonitrile is faster than propionitrile. Furthermore, the coupling reaction in acetonitrile allows greater formation of the IVa β anomer. Several solvents were studied in the coupling reaction of dibenzyl 4'-demethyl-4-epipodophyllotoxin-4'-phosphate and 2,3-O-benzyl-4,6-O-ethylidene-α,β-D-glucopyranose. Typically, the β:α ratio increased with higher dielectric constant of the solvent.

The substituents on the substituted benzyl protecting groups on the glucopyranose also influence the ratio of formation of IVa β to IVa α. For example, bulky groups in the ortho position favor the C-1"-β form of Compound IV by creating steric hindrance in Compound IVα while little hindrance is caused by meta and para substituents. Electron withdrawing groups also favored the C-1"-β anomer. The highest β:α ratio is obtained with pentafluorobenzyl, which produced a IVa C-1"-β to IVa C-1"-α ratio of 80:20.

The anomeric mixture of IVa α,β is separated to obtain substantially pure C-1"-β form by a single crystallization step after standard work-up. The anomeric mixture of IVa α,β is dissolved in methanol. The solution is heated to reflux to completely dissolve the compound IVa α,β. The solution is allowed to cool to room temperature. The resulting precipitate is the substantially pure C-1"-β form of Compound IVa.

In preferred embodiments, the crystallization to obtain the C-1"-β form of Compound IVa is carried out directly with the coupling reaction. After the coupling reaction is completed and without further extraction or standard work-up, methanol is added to the solution and the solution is allowed to warm to 0° C. The solution is then allowed to stand at 0° C. for several hours. The resulting solid has been found to be substantially pure IVa C-1"-β.

The ability to directly crystallize the C-1"-β anomer of Compound IVa even from a 50:50 anomeric mixture is a significant and unexpected advantage of the process. As reported in J. March, *Advanced Organic Chemistry*, 4th Ed., John Wiley and Sons, New York, 1992, p. 121, very few diastereomers are able to be separated by a single crystallization.

After recovery of the C-1"-β anomer of Compound IV, the hydroxy and the phosphate protecting groups are removed simultaneously by known methods and preferably by hydrogenation. The hydrogenation deprotection step proceeds efficiently to produce etoposide phosphate in high yields with minimal degradation. Compounds IV, IVa and IVb are very labile and sensitive to both acid and base. Existing processes of using acids or bases to remove the hydroxy and phosphate protecting groups usually result in decomposition of a portion of the desired product. In addition, the deprotection steps can cleave the ethylidene group from the glucopyranose. Compared to existing processes for removing the protecting groups, the hydrogenation process is advantageous in that only one deprotection step is required, no heavy metals are required, and the process is conducted under mild, neutral conditions to give a high yield. Chromatography is not required to obtain etoposide phosphate in pure form as in other processes.

The hydrogenation may be by a number of known processes. Typically, the hydrogenation is in the presence of a noble metal catalyst in a suitable solvent or solvent mixture.

In preferred embodiments, the hydrogenation is carried out using 4% palladium on carbon in a solution of Compound IVa C-1"-β in 50/50 methanol/tetrahydrofuran (THF). The mixture is hydrogenated for several hours, typically 3–6 hours, at 40–50 psig hydrogen. The catalyst may then be removed by filtering, and the etoposide phosphate recrystallized from ethanol. The deprotection of IV C-1"-β to etoposide phosphate of Formula V is as follows:

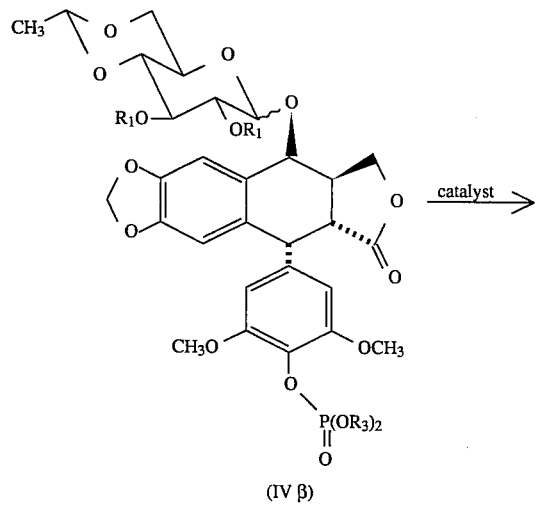

(IV β)

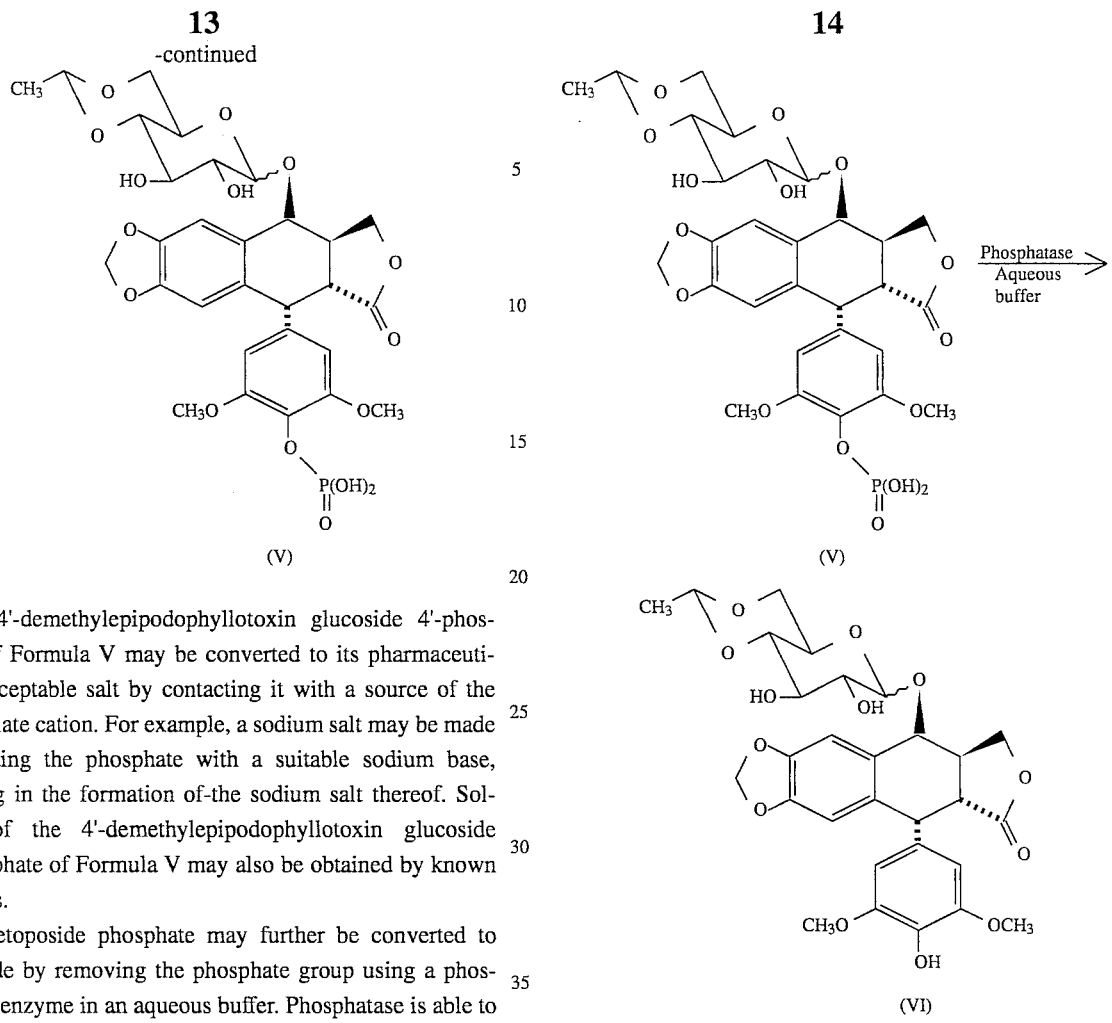

The 4'-demethylepipodophyllotoxin glucoside 4'-phosphate of Formula V may be converted to its pharmaceutically acceptable salt by contacting it with a source of the appropriate cation. For example, a sodium salt may be made by treating the phosphate with a suitable sodium base, resulting in the formation of-the sodium salt thereof. Solvates of the 4'-demethylepipodophyllotoxin glucoside 4'-phosphate of Formula V may also be obtained by known methods.

The etoposide phosphate may further be converted to etoposide by removing the phosphate group using a phosphatase enzyme in an aqueous buffer. Phosphatase is able to convert etoposide phosphate completely to etoposide. The reaction is carried out in a tank with a buffer at a pH of about 5–12 and preferably at pH 6–9 at room temperature. Typically, etoposide phosphate is in the form of a solvate when mixed with the aqueous buffer.

The enzymatic conversion of etoposide 4'-phosphate to etoposide is advantageous since the conversion is carried out under mild conditions without degradation of the etoposide or etoposide 4'-phosphate. For example, the labile ethylidene group is substantially unaffected by the phosphatase enzyme. The enzyme may be any enzyme having phosphatase activity at pH 5–12 and preferably pH 6–9. Suitable phosphatase enzymes include acid and alkaline phosphatase. The phosphatase may be obtained from bovine, bacterial or other sources such as bovine and calf intestinal mucosa. Alternatively, the phosphatase may be wheat germ lipase which is known to have phosphatase activity. These enzymes are available from Sigma Chemical Company.

Suitable buffers, for example, include M-Tris pH 7.8, M-Tris pH 8.7, M-Borate pH 10.0 and M-Bicarbonate pH 10.3. The dephosphorylation of Etoposide phosphate V to Etoposide VI is as follows:

The following non-limiting examples demonstrate preferred embodiments of the invention.

EXAMPLE 1

2,3-Di-O-benzyl-4,6-O-ethylidene-α,β-D-glucopyranose (IIIa α,β). This compound was prepared according to adaptation of literature procedures for analogous compounds as disclosed in U.S. Pat. No. 4,997,931. $^1$H NMR showed the anomeric composition to be 57:43 β:α. $R_f$ (40% EtOAc/hexane): 0.40. $^1$H NMR (CDCl$_3$): δ7.39–7.27 (m, 10H), 5.14 (d, 0.5H, J=3.7 Hz), 4.91–4.66 (m, 5.5H), 4.14 (dd, 0.5H, J=5.0, 10.5 Hz), 4.09 (dd, 0.5H, J=5.0, 10.3 Hz), 3.94–3.88 (m, 1H), 3.66 (t, 0 .5H, J=9.0 Hz), 3.56–3.25 (m, 3.5H), 3.10 (bs, 1H, conc. dependent OH), 1.36 (d, 3H, J=5.0 Hz). $^{13}$C NMR (CDCl$_3$) : δ128.53, 128.42, 128.31, 128.09, 127.95, 127.83, 127.63, 99.50, 97.72, 92.12, 82.94, 81.44, 81.08, 80.89, 79.31, 78.33, 75.23, 75.12, 74.96, 73.81, 68.53, 68.22, 66.22, 62.48, 20.43.

EXAMPLE 2

2,3-Di-O-benzyl-4,6-O-ethylidene-β-D-glucopyranose (IIIa β). The anomeric mixture IIIa α,β (7 g) was placed in a 250 ml roundbottom flask. Hexane (125 ml) was added, and the suspension was heated to reflux. The sugar became an insoluble oil which sank to the bottom. The suspension was allowed to cool to room temperature, then a stir bar was added and the solution was gently stirred overnight. White, fluffy crystals formed and floated in the hexane above the rest of the impure solid. The crystals were collected by decanting the supernatant into a Buchner funnel. The impure solid was left in the flask. The white solid IIIa β was dried at room temperature under vacuum (20 mm Hg). $^1$H NMR (CDCl$_3$): δ7.37–7.27 (m, 10H), 4.90–4.69 (m, 6H), 4.14 (dd, 1H, J=4.9, 10.4 Hz), 3.66 (t, 1H, J=9.0 Hz), 3.54 (t, 1H, J=10.2 Hz), 3.45 (t, 1H, J=9.3 Hz), 3.37–3.27 (m, 2H), 3.23 (d, 1H, J=5.5 Hz, conc. dependent OH), 1.36 (d, 3H, J=5.1Hz). $^{13}$C NMR (CDCl$_3$): δ128.42, 128.29, 128.11, 127.93, 127.82, 127.63, 99.45, 97.71, 82.93, 81.06, 80.88, 75.22, 74.96, 68.21, 66.21, 20.39.

EXAMPLE 3

Dibenzyl 4'-demethyl-4-epipodophyllotoxin-4'-phosphate (IIa). An oven-dried, three-neck 1L roundbottom flask was fitted with a dropping funnel, stir bar, thermometer, two septa, and N$_2$ inlet. The flask was charged with 4'-demethylepipodophyllotoxin (I, 25.00 g, 62.45 mmol) and anhydrous acetonitrile (367 ml, 0.17M). The suspension was cooled to −10° C. Carbon tetrachloride (30.1 ml, 312.25 mmol) was added, keeping the temperature at −10° C. N,N-Diisopropylethylamine (22.84 ml, 131.15 mmol) was added by syringe over 3 minutes. N,N-dimethylaminopyridine (0.763 g, 6.25 mmol) was added all in one portion, followed by the dropwise addition of dibenzyl phosphite (20.00 ml, 90.55 mmol) over a 15 minute period. The reaction was somewhat exothermic during the addition, but the internal temperature was kept at 10° C. with additional external cooling. The reaction was stirred at −10° C. for 37 minutes. During this time, the starting material dissolved and the reaction was followed by HPLC. 0.5M KH$_2$PO$_4$ (150 ml) was added and the solution was allowed to warm to room temperature. The mixture was extracted with EtOAc (1× 350 ml) and then washed with water (2×100 ml). The organic layer was dried over Na$_2$SO$_4$ and concentrated in vacuo to a volume of 150 ml. 2-Propanol (500 ml) was added. Solvent (200 ml) was removed in vacuo and solid precipitated during this time. 2-Propanol (500 ml) was added and then another 550 ml of solvent was removed in vacuo. Finally, 2-propanol (250 ml) was added and the mixture was heated to reflux until all solid dissolved. The yellow solution was cooled to room temperature and then to 0° C. for 4 hours. A white solid was collected, washed twice with cold 2-propanol and dried in vacuo (40° C., 20 mm Hg) to yield 37.15 g (90.1%). HPLC R$_t$ R$_f$ (10% MeOH/CH$_2$Cl$_2$): 0.66. $^1$H NMR (CDCl$_3$): δ7.37–7.28 (m, 10H), 6.81 (s, 1H), 6.39 (s, 1H), 6.30 (s, 2H), 5.90 (dd, 2H, J=1.0, 12.7 (Hz), 5.28–5.14 (m, 4 H), 4.71 (d, 1H, J=3.4 Hz), 4.53 (d, 1H, J=5.1Hz), 4.25 (dd, 1H, J=8.7, 10.7 Hz), 3.63 (s, 6H), 3.27 (dd, 1H, J=5.2, 14.1 Hz), 2.71–2.61 (m, 1H). $^{13}$C NMR (CDCl$_3$): δ175.27, 151.15, 151.11, 148.22, 147.32, 137.28, 136.04, 135.94, 132.19, 131.35, 128.43, 128.30, 128.26, 127.69, 127.64, 110.13, 109.32, 107.66, 101.45, 69.62, 69.53, 69.46, 67.75, 66.17, 56.06, 43.81, 40.39, 38.47.

EXAMPLE 4

Dibenzyl 4-(2,3-di-O-benzyl-4,6-O-ethylidene-β-D-glucopyranosyl)- 4'-demethyl-4-epipodophyllotoxin-4'-phosphate (IVa β) (coupling in acetonitrile). An oven-dried 25 ml two-neck roundbottom flask fitted with a stir bar, thermometer, septa, and N$_2$ inlet was charged with dibenzyl 4'-demethyl-4-epipodophyllotoxin-4'-phosphate (IIa, 1.00 g, 1.51 mmol), dry 4A molecular sieves (¹⁄₁₆" pellet) (2.0 g), 2,3-di-O-benzyl-4,6-O-ethylidene-α,β-D-glucose (IIIa β,α, 85:15, 0.702 g, 1.817 mmol), and anhydrous acetonitrile (10.0 ml). The solution was stirred until homogeneous and then cooled to −20° C. Boron trifluoride etherate (0.50 ml, 4.08 mmol) was added dropwise over 2 minutes. The reaction was held at −20° C. for 80 minutes. White solid began precipitating 45 minutes after addition of BF$_3$. Pyridine (5.23 ml, 64.7 mmol) was added. The suspension was allowed to warm to room temperature and was diluted with CH$_2$Cl$_2$ (10 ml). The white solid dissolved. The solution was filtered to remove remaining solids. The solution was washed with 3% HCl (7 ml), and then the aqueous phase was back extracted with CH$_2$Cl$_2$ (10 ml). The combined organic phase was washed with water (7 ml) and the aqueous phase was back extracted with CH$_2$Cl$_2$ (10 ml). The combined organic phase was washed finally with saturated NaCl (7 ml). The organic layer was dried over Na$_2$SO$_4$ and concentrated in vacuo to a white/yellow solid. HPLC of the crude product showed a 71.6:28.4 ratio of IVa β:IVa α. The solid was dissolved in CH$_2$Cl$_2$ (10 ml) with stirring. Methanol (90 ml) was added. Some solid soon precipitated out. The solution was warmed to reflux with stirring, during which time the solid dissolved, and then 20 ml of solvent was distilled off. The solid began crystallizing after 19 ml was collected. The mixture was allowed to cool to room temperature while stirring gently for 5 hours. The white solid was collected and rinsed twice with room temperature methanol. The solid IVa β was dried in vacuo (40° C., 20 mm Hg) and yielded 0.830 g (53.3%). R$_f$ (50% EtOAc hexane): 0.36. $^1$H NMR (CDCl$_3$): δ7.38–7.18 (m, 18 H), 7.00–6.98 (m, 2H), 6.82 (s, 1H), 6.54 (s, 1H), 6.25 (s, 2H), 5.97–5.89 (dd, 2H, J=1.0, 26.7 Hz), 5.29–5.18 (m, 4H), 4.89–4.85 (m, 2H), 4.77–4.71 (m, 3H), 4.60–4.49 (m, 3H), 4.39 (t, 1H, J=10.2 Hz), 4.23 (t, 1H, J=8.2 Hz), 4.16 (dd, 1H, J=4.9, 10.4 Hz), 3.63 (s, 6H), 3.55 (t, 1H, J=10.2 Hz), 3.45–3.34 (m, 2H), 3.32–3.21 (m, 2H), 2.89– 2.80 (m, 1H), 1.38 (d, 3H, J=5.0 Hz). $^{13}$C NMR (CDCl$_3$): δ174.74, 151.20, 148.72, 147.17, 138.48, 137.75, 137.0, 136.3, 136.2, 132.02, 128.62, 128.42, 128.30, 128.21, 128.07, 127.87, 127.70, 127.67, 110.72, 109.18, 107.73, 102.32, 101.60, 99.55, 81.66, 80.95, 75.40, 75.06, 73.45, 69.45, 68.19, 67.87, 65.97, 43.87, 41.22, 37.48, 20.40.

The C-1"-α isomer IVα remained in the mother liquor, along with some of the desired product IVβ (IVβ:IVα 13.7:86.3).

EXAMPLE 5

Dibenzyl 4-(2,3-di-O-benzyl-4,6-O-ethylidene-β-D-glucopyranosyl)- 4'-demethyl-4-epipodophyllotoxin-4'-phosphate (IVa β) (coupling in dichloroethane). An oven-dried 250 ml three-neck roundbottom flask fitted with a stir bar, thermometer, two septa and N$_2$ inlet was charged with dibenzyl 4'-demethyl-4-epipodophyllotoxin-4'-phosphate (IIa, 14.295 g, 21.57 mmol), dry 4A molecular sieves (¹⁄₁₆" pellet) (28.6 g), 2,3-di-O-benzyl-4,6-O-ethylidene-α ,β-D-glucose (IIIa α,β, 10.0 g, 25.88 mmol), and anhydrous 1,2-dichloroethane (143 ml). The solution was stirred until homogenous and then cooled to −20° C. Boron trifluoride etherate (7.15 ml, 58.24 mmol) was added dropwise over 10 minutes. The reaction was held at −20° C. for 18 hours. Pyridine (5.23 ml, 64.7 mmol) was added and the mixture turned from brown to yellow. The cloudy solution was allowed to warm to room temperature and was diluted with CH$_2$Cl$_2$ (200 ml) and filtered to remove solids. The solution was washed with 3% HCl (100 ml), water (100 ml) and finally saturated NaCl (100 ml). The organic layer was dried over Na$_2$SO$_4$ and concentrated in vacuo to a yellow oil.

Refluxing methanol (1500 ml) was added while stirring. The mixture was allowed to cool to room temperature and stand overnight. The white solid was collected and rinsed twice with methanol. The solid IVa β was dried in vacuo (40° C., 20 mm Hg) and yielded 8.86g (39.8%).

The C-1"-α isomer IVa α remained in the mother liquor, along with some of the desired product IVa β. This remaining coupled product was recovered by further crystallization and/or chromatography. The ratio of β:α of the crude product before crystallization of IVβ was 54:46. The overall yield of coupled product was 81%.

Dibenzyl 4-(2,3-di-O-benzyl-4,6-O-ethylidene-α-D-glucopyranosyl)- 4'-demethyl-4-epipodophyllotoxin-4'-phosphate (IVa α): $R_f$ (50% EtOAc/hexane): 0.31. $^1$H NMR (CDCl$_3$): δ7.38–7.21 (m, 20H), 6.87 (s, 1H), 6.26 (s, 2H), 5.95 (d, 2H, J=5.8 Hz), 5.29–5.18 (m, 4H), 4.87 (dd, 3H, J=2.3, 11.1 Hz), 4.79–4.74 (m, 2H), 4.68–4.58 (m, 4 H), 4.11 (t, 1H, J=7.9 Hz), 3.95 (q, 1H, J=10.6 Hz), 3.86 (t, 1H, J=9.2 Hz), 3.63 (s, 6H), 3.51 (dd, 1H, J=3.6, 9.4 Hz), 3.45 (d, 1H, J=7.2 Hz), 3.45–3.35 (m, 3H), 2.82–2.75 (m, 1H), 1.32 (d, 3H, J=5.0 Hz). $^{13}$C NMR (CDCl$_3$): δ174.91, 151.22, 151.18, 148.44, 147.02, 138.56, 137.83, 137.05, 136.27, 136.18, 132.19, 129.27, 128.59, 128.45, 128.34, 128.24, 128.12, 127.96, 127.89, 127.72, 127.69, 110.44, 109.81, 107.85, 101.61, 101.08, 99.59, 82.07, 79.36, 78.59, 76.76, 75.09, 74.69, 69.52, 69.46, 69.41, 68.18, 67.04, 62.95, 56.15, 43.82, 41.10, 38.41, 20.40.

EXAMPLE 6

This example demonstrates coupling and crystallization steps being carried out in the same reaction vessel. A 50 ml three-neck roundbottom flask with a stir bar was oven-dried, fitted with two septa, and cooled under N$_2$. Dibenzyl 4'-demethyl-4-epipodophyllotoxin- 4'-phosphate (1.002 g, 1.51 mmol) and 2,3-O-benzyl-4,6-O-ethylideneglucopyranose (IIa 85:15 β:α, 0.702 g, 1.81 mmol) were added. The solids were dissolved in anhydrous acetonitrile (10.0 ml), and then the solution was cooled to −40° C. Boron trifluoride etherate (0.50 ml, 4.1 mmol) was added dropwise. The solution was stirred at −40° C. and followed by HPLC. During the reaction, some product precipitated. After 6 hours, methanol (30 ml) was added dropwise. The suspension was allowed to warm to −30° C. with stirring, then allowed to stand at 0° C. without stirring for 17 hours. The solid was collected in a Buchner funnel and rinsed twice with room temperature methanol. This produced 0.9668 g (62.0%) of IVa β with HI (homogeneity index) of 100%.

EXAMPLE 7

Etoposide-4'-phosphate (V): 4% Palladium on carbon, 50% wet (314 mg) was added to a solution of dibenzyl 4-( 2,3-di-O-benzyl-4,6-O-ethylidene-β-D-glucopyranosyl)-4'-demethyl- 4-epipodophyllotoxin-4'-phosphate (IVa β, 758 mg) in 50/50 MeOH/THF (50 ml). The mixture was hydrogenated at ambient temperature and 40–50 psig hydrogen for 3–6 hours. The catalyst was filtered off and rinsed with MeOH. The filtrate was concentrated in vacuo (40°–60° C., aspirator) to a volume of 8–10 ml. Absolute ethanol (50 ml) was added and the solution was again concentrated to −10 ml. Ethanol (25 ml) was again added and the solution was concentrated to 10 ml. Seed crystals of etoposide-4'-phosphate diethanol solvate were added and the temperature of the solution was adjusted from about 50° C. to 15°–20° C. over 30–60 minutes. After holding at 15°–20° C. another 30 minutes, the white crystals were collected by filtration and washed with 5° C. ethanol (5–10 ml). The solid was dried under high vacuum at 25°– 40° C. There was obtained 436 mg (77.8%) of etoposide-4'-phosphate diethanol solvate (V) which assayed at 99.2 area % purity by HPLC.

EXAMPLE 8

Etoposide (VI): With magnetic stirring, etoposide-4'-phosphate diethanol solvate (V, 410 mg) was dissolved in 1.0M Tris buffer (8.0 ml). The pH was adjusted from 8.1 to 8.7 with 1N NaOH. The solution was warmed to 35° C. A solution (2.0 ml, 200 units/ml) of alkaline phosphatase (Sigma, catalog #P6774) in MilliQ water was added. Within 10 minutes, solids precipitated. The pH was maintained in the range 8.4–8.8 by adding 1N NaOH as needed. The reaction was followed by HPLC. After 3 hours, the mixture was cooled to 10° C. for 15 minutes. The solid was collected by vacuum filtration, washed with water (5–7 ml), and dried under high vacuum (20° C.) for 18 hours. There was obtained 241 mg (76% of etoposide (VI), 95.5 area % by HPLC.

What is claimed is:

1. A process for preparing a compound having the Formula Va

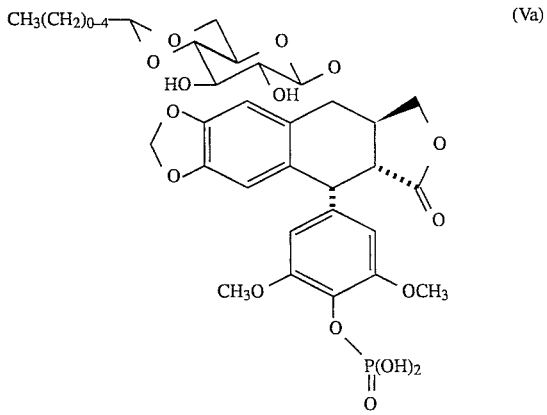

which comprises reacting an anomeric mixture of a compound of Formula IIIb

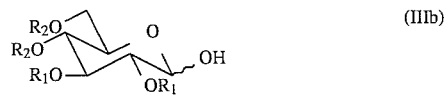

wherein $R_1$ is an arylmethyl hydroxy protecting group and $R_2$ is arylmethyl or the two $R_2$ groups together are $C_{1-5}$ alkylidene with a compound of Formula II in an organic solvent as a reaction medium and in the presence of a Lewis acid at or below room temperature

19

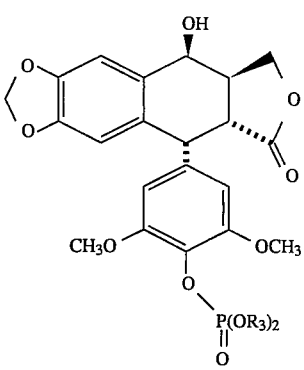

where $R_3$ is arylmethyl and where $R_1$, $R_2$ and $R_3$ are the same or different to form an anomeric mixture of the compound of Formula IVb

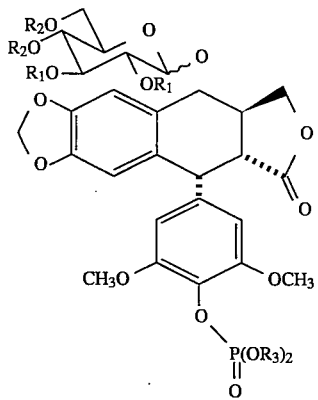

and adding an alcohol to said reaction medium and crystallizing and separating the C-1"-$\beta$ form of Compound IVb substantially free of the $\alpha$ form directly from said anomeric mixture in said reaction medium, and subsequently removing the hydroxy and phosphate protecting groups and in cases where $R_2$ is arylmethyl, reacting Compound IVb with a carbonyl having one to five carbon atoms or an acetal equivalent thereof.

2. The process of claim 1, wherein $R_1$ and $R_3$ are benzyl or a benzyl substituted with one or more substituents selected from the group consisting of $C_{1-4}$ alkyl, hydroxy, phenyl, benzyl, halogen, alkoxy nitro, carboxylic acids and esters thereof.

3. The process of claim 1, wherein said hydroxy and phosphate protecting groups are removed simultaneously.

4. The process of claim 1, wherein said hydroxy and phosphate protecting groups are simultaneously removed by hydrogenating at ambient temperature in the presence of a noble metal catalyst.

5. The process of claim 4, wherein said noble metal catalyst is palladium.

6. The process of claim 1, wherein said alcohol is methanol.

7. The process of claim 1, wherein said Lewis acid is boron trifluoride etherate.

8. The process of claim 1, comprising reacting Compound II with Compound IIIb in a halogenated or non-halogenated solvent.

9. The process of claim 8, wherein said solvent is acetonitrile.

10. The process of claim 9, wherein said solvent contains a metal perchlorate to increase the ionic strength of the solvent.

11. The process of claim 1, further comprising preparing said compound of Formula II by reacting a phenol of

20

Formula I

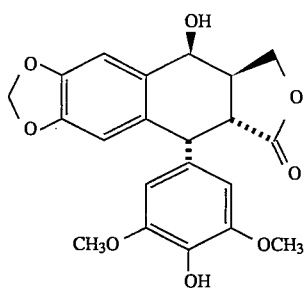

with a di(arylmethyl)phosphite, tetrahalomethane, trialkylamine and an acylation catalyst to form the protected phosphate of Formula II.

12. The process of claim 1, wherein said reaction is carried out at about room temperature to –40° C.

13. A compound having the Formula IV

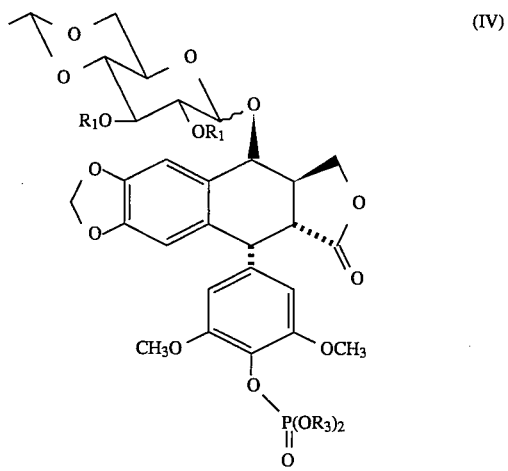

wherein $R_1$ is a benzyl or substituted benzyl hydroxy protecting group and $R_3$ is a benzyl or substituted benzyl phosphate protecting group.

14. The compound of claim 13, wherein $R_1$ and $R_3$ are a benzyl substituted with one or more selected from the group consisting of $C_{1-4}$ alkyl, hydroxy, phenyl, benzyl, halogen, alkoxy, nitro, carboxylic acids and esters thereof.

15. A process of obtaining the C-1"-$\beta$ anomer of Formula IVa

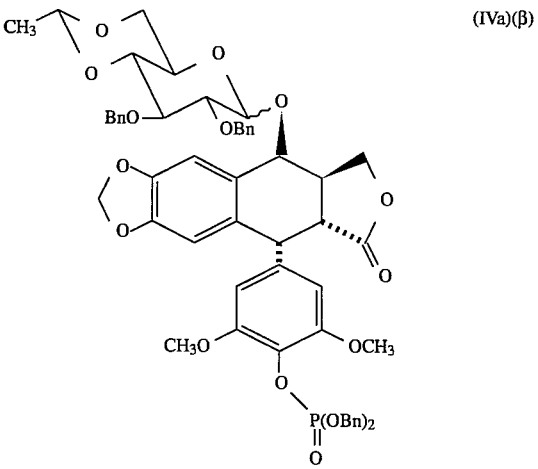

said process comprising forming a solution of an anomeric mixture of a compound of Formula IV in an organic solvent

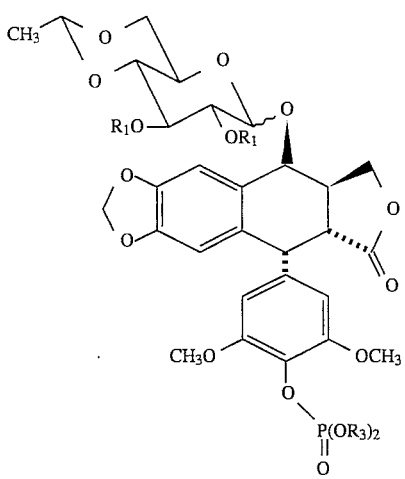

(IV)

where $R_1$ and $R_3$ are benzyl, adding an alcohol to said solvent and crystallizing said C-1"-β anomer from said anomeric mixture in said solution and recovering said crystals of the C-1"-β anomer of Formula IVa substantially free of the α anomer from said anomeric mixture.

16. The process of claim 15 wherein said solvent is acetonitrile.

17. The process of claim 15, wherein said solvent is an alcohol and said process comprises heating said alcohol to reflux to dissolve said anomeric mixture, and cooling said solution to crystallize said C-1"-β anomer of Formula IVa.

18. The process of claim 15 wherein said alcohol is methanol.

19. The process of claim 4, wherein said hydroxy and phosphate protecting groups are removed by hydrogenating at ambient temperature in a 50/50 methanol-tetrahydrofuran solvent in the presence of a 4% palladium on carbon catalyst by contacting compound IVb with hydrogen at 40–50 psig.

20. The process of claim 1, further comprising adding methanol to said anomeric mixture of the compound of Formula IVb to dissolve said compound of Formula IVb, heating the resulting solution to reflux, and cooling said solution to room temperature to precipitate and separate said C-1"-β anomer of compound IVb from the solution of said anomeric mixture.

21. The process of claim 1, comprising reacting compounds IIIb and II at about room temperature to − 40° C., and wherein said crystallizing step comprises adding methanol to said reaction medium and warming said reaction medium to about 0° C. to precipitate and separate said C-1"-β anomer of Compound IVb from said anomeric mixture.

22. The process of claim 1, comprising reacting compounds IIIb and II in acetonitrile at about room temperature to −40° C. in the presence of boron trifluoride etherate.

23. The process of claim 22, comprising reacting about 1.2 mole of compound IIIb per mole of compound II.

24. The process of claim 11, comprising reacting compound I with dibenzyl phosphite, carbon tetrachloride, N,N dimethylaminopyridine at about −10° C. in acetonitrile, the carbon tetrachloride being present in the amount of 1 or more equivalents per equivalent of compound I.

25. The process of claim 24, comprising reacting compound I with about 1.4 moles of dibenzyl phosphite, 5 moles of carbon tetrachloride, 2.1 moles of N,N diisopropylethylamine and 0.1 mole of N,N-dimethylaminopyridine per mole of Compound I.

26. The process of claim 12, comprising reacting compound II and IIIb at about −10° C.

27. The process of claim 15, comprising forming a solution of an anomeric mixture of compound IVa in acetonitrile, adding methanol to said solution, heating to reflux and cooling said solution to crystallize and separate said C-1"-β anomer of compound IVa from the solution of said anomeric mixture.

28. A process for preparing a compound having the Formula V

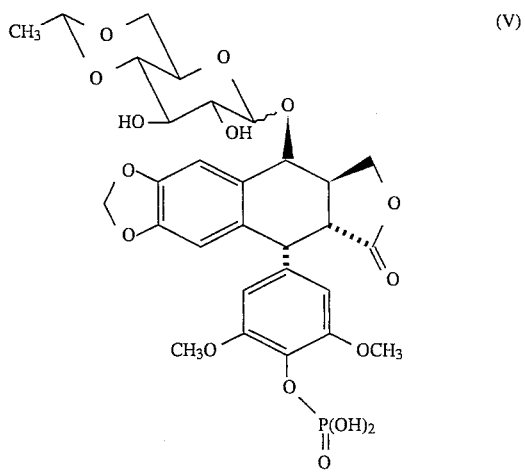

(V)

which comprises reacting an anomeric mixture of a compound of Formula IIIa

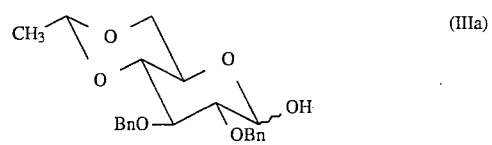

(IIIa)

with a compound of Formula II in an organic solvent reaction medium and in the presence of a Lewis acid selected from the group consisting of boron trifluoroetherate, $AlCl_3$, $ZnCl_2$, $Et_2AlCl$, $CF_3SO_3H$, $CF_3SO_3Ag$, $Zn(CF_3SO_3)_2$ and $TMSCF_3SO_3$ at or below room temperature

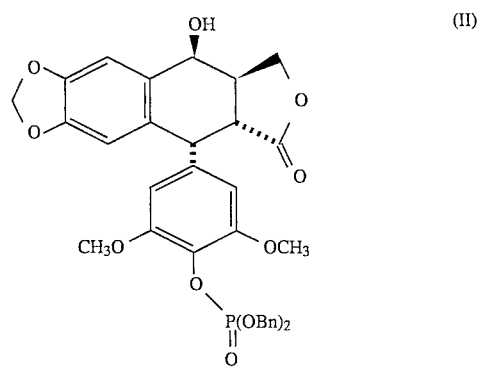

(II)

to form an anomeric mixture of the compound of Formula IVa

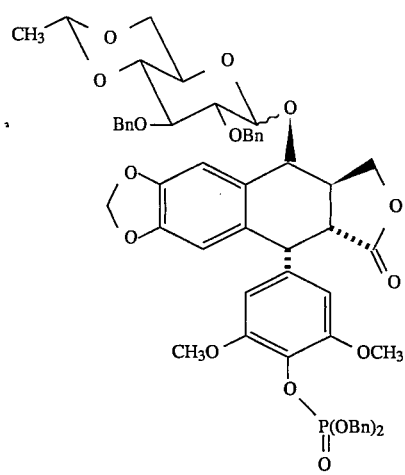

(IVa α,β)

adding an alcohol to said reaction medium and crystallizing and separating the C-1"-β form of Compound IVa from a solution of said anomeric mixture, and subsequently removing the benzyl protecting groups.

29. The process of claim 28, wherein said reaction medium is acetonitrile, and said process comprises reacting compounds IIIa and II at about room temperature to –40° C.

30. The process of claim 28, wherein after reacting compounds II and IIIa, said process comprising adding a solvent to the resulting anomeric reaction mixture, heating the anomeric mixture to dissolve the compound IVa and cooling the mixture to crystallize and Separate the C-1"-β form of compound IVa from said anomeric mixture, wherein said solvent is selected from the group consisting of methanol and a mixture of methylene chloride and methanol.

31. The process of claim 30, comprising heating said anomeric mixture to reflux to dissolve said compound IVa and cooling to room temperature to crystallize and separate said C-1"-β form of compound IVa from said anomeric mixture.

32. The process of claim 28, wherein after reacting compounds II and IIIa, adding methanol to the resulting anomeric reaction mixture to dissolve the compound IVa and crystallizing and separating said C-1"-β form of compound IVa from the anomeric mixture.

33. The process of claim 28, wherein said step of removing the benzyl protecting groups comprises hydrogenating at ambient temperature in a 50/50 methanol tetrahydrofuran solvent in the presence of a 4% palladium on carbon catalyst by contacting compound IVa with hydrogen at 40–50 psig.

* * * * *